United States Patent
Diel et al.

(10) Patent No.: US 11,013,566 B2
(45) Date of Patent: May 25, 2021

(54) FORCE TRANSMISSION MECHANISM FOR SURGICAL INSTRUMENT, AND RELATED SYSTEMS AND METHODS

(71) Applicant: Intuitive Surgical Operations, Inc., Sunnyvale, CA (US)

(72) Inventors: Mark A. Diel, Menlo Park, CA (US); Bram Gilbert Antoon Lambrecht, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 666 days.

(21) Appl. No.: 15/503,313

(22) PCT Filed: Aug. 13, 2015

(86) PCT No.: PCT/US2015/045036
§ 371 (c)(1),
(2) Date: Feb. 10, 2017

(87) PCT Pub. No.: WO2016/025700
PCT Pub. Date: Feb. 18, 2016

(65) Prior Publication Data
US 2017/0231703 A1 Aug. 17, 2017

Related U.S. Application Data

(60) Provisional application No. 62/037,897, filed on Aug. 15, 2014.

(51) Int. Cl.
*A61B 34/35* (2016.01)
*A61B 34/00* (2016.01)
(Continued)

(52) U.S. Cl.
CPC ........ *A61B 34/35* (2016.02); *A61B 17/00234* (2013.01); *A61B 34/70* (2016.02);
(Continued)

(58) Field of Classification Search
CPC .............. A61B 17/00234; A61B 17/29; A61B 2017/00389; A61B 2017/2902;
(Continued)

(56) References Cited

U.S. PATENT DOCUMENTS 1,361,154 A * 12/1920 Henderson .............. F16H 1/166
384/508
1,470,718 A * 10/1923 Forsyth ................... F16H 1/166
74/464
(Continued)

FOREIGN PATENT DOCUMENTS

CN 2171319 Y 7/1994
DE 2120897 A1 * 11/1971 ............. F16H 1/166
(Continued)

OTHER PUBLICATIONS

Extended European Search Report for Application No. EP15831744. 6, dated Feb. 14, 2018, 8 pages.
(Continued)

*Primary Examiner* — Joseph Brown
(74) *Attorney, Agent, or Firm* — Jones Robb, PLLC

(57) ABSTRACT

A force transmission mechanism for a surgical instrument includes a worm drive, a lever arm, and an actuation element. The lever arm may include a follower member at a first end of the lever arm. The follower member engages the worm drive and is configured to be driven by the worm drive. The actuation element is connected the lever arm. The actuation element is configured to transmit force to actuate an end effector of the surgical instrument. Rotational movement of the worm drive imparts translational movement to the actuation element via the lever arm.

20 Claims, 13 Drawing Sheets

(51) Int. Cl.
  *B25J 15/00*  (2006.01)
  *B25J 15/02*  (2006.01)
  *B25J 9/10*  (2006.01)
  *A61B 17/00*  (2006.01)
  *F16H 25/08*  (2006.01)
  *A61B 17/29*  (2006.01)
  *A61B 90/00*  (2016.01)

(52) U.S. Cl.
  CPC .............. *A61B 34/71* (2016.02); *B25J 9/109* (2013.01); *B25J 15/0028* (2013.01); *B25J 15/0226* (2013.01); *F16H 25/08* (2013.01); *A61B 2017/00398* (2013.01); *A61B 2017/2902* (2013.01); *A61B 2017/294* (2013.01); *A61B 2017/2943* (2013.01); *A61B 2017/2944* (2013.01); *A61B 2090/034* (2016.02)

(58) Field of Classification Search
  CPC .... A61B 2017/2932; A61B 2017/2933; A61B 2017/294; A61B 2017/2943; A61B 2017/2944; A61B 34/35; A61B 34/70; A61B 2017/2916; B25J 15/0213; B25J 15/0226; F16H 25/12; F16H 25/122; F16H 25/125; F16H 25/2409
  See application file for complete search history.

(56) References Cited

U.S. PATENT DOCUMENTS

| | | | |
|---|---|---|---|
| 7,950,560 B2 | 5/2011 | Zemlok et al. | |
| 8,545,515 B2 | 10/2013 | Prisco et al. | |
| 9,055,961 B2 * | 6/2015 | Manzo | A61B 18/1445 |
| 2010/0001036 A1 * | 1/2010 | Marczyk | A61B 17/07207 |
| | | | 227/175.1 |
| 2010/0217405 A1 | 8/2010 | Bravo | |
| 2011/0000331 A1 * | 1/2011 | Iwase | F16H 1/163 |
| | | | 74/425 |
| 2011/0071544 A1 | 3/2011 | Steger et al. | |
| 2012/0089154 A1 | 4/2012 | Green et al. | |
| 2012/0104071 A1 * | 5/2012 | Bryant | A61B 17/07207 |
| | | | 227/175.1 |
| 2012/0221018 A1 * | 8/2012 | Bastia | A61B 17/3468 |
| | | | 606/139 |
| 2012/0310254 A1 | 12/2012 | Manzo et al. | |
| 2013/0282021 A1 * | 10/2013 | Parihar | A61B 17/105 |
| | | | 606/130 |
| 2013/0325031 A1 | 12/2013 | Schena et al. | |
| 2013/0325033 A1 | 12/2013 | Schena et al. | |
| 2014/0005680 A1 | 1/2014 | Shelton, IV et al. | |
| 2014/0114327 A1 * | 4/2014 | Boudreaux | A61B 18/1445 |
| | | | 606/130 |
| 2014/0338477 A1 * | 11/2014 | Donlon | F16H 19/02 |
| | | | 74/89.14 |
| 2016/0175062 A1 * | 6/2016 | Limon | A61B 34/30 |
| | | | 134/32 |

FOREIGN PATENT DOCUMENTS

| | | | | |
|---|---|---|---|---|
| DE | 19623222 A1 * | 12/1997 | | F16H 1/24 |
| EP | 2108339 A1 | 10/2009 | | |
| GB | 639967 A * | 7/1950 | | A61C 3/06 |
| WO | 0238342 A1 | 5/2002 | | |
| WO | WO-0238342 A1 * | 5/2002 | | B25J 15/0206 |
| WO | WO-2014186412 A2 | 11/2014 | | |

OTHER PUBLICATIONS

International Search Report and Written Opinion for Application No. PCT/US15/045036, dated Nov. 16, 2015, 12 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

FORCE TRANSMISSION MECHANISM FOR SURGICAL INSTRUMENT, AND RELATED SYSTEMS AND METHODS

RELATED APPLICATIONS

This patent application is a U.S. national stage application under 35 U.S.C. § 371(c) of International Application No. PCT/US2015/045036, filed on Aug. 13, 2015, which claims priority to and the benefit of the filing date of U.S. Provisional Patent Application 62/037,897, entitled "FORCE TRANSMISSION MECHANISM FOR SURGICAL INSTRUMENT, AND RELATED SYSTEMS AND METHOD," filed Aug. 15, 2014, each of which is incorporated by reference herein in its entirety.

TECHNICAL FIELD

Aspects of the present disclosure relate to a mechanical force transmission mechanism that includes a component for converting rotational input to a translational output. For example, aspects of the present disclosure relate to force transmission mechanism components for converting rotational input to a translational movement along a shaft of a surgical instrument to actuate a gripping end effector.

BACKGROUND

Benefits of minimally invasive surgery are well known, and they include less patient trauma, less blood loss, and faster recovery times when compared to traditional, open incision surgery. In addition, the use of teleoperated surgical systems (e.g., systems operating surgical instruments at least in part with computer assistance, such as instruments operated with robotic technology), such as the da Vinci® Surgical System commercialized by Intuitive Surgical, Inc. of Sunnyvale, Calif. is known. Such teleoperated surgical systems allow a surgeon to operate with intuitive control and increased precision when compared to manual minimally invasive surgeries.

To perform actions directed by a surgeon, a surgical instrument may use one or more actuation elements to move the surgical instrument. For instance, actuation elements are used to provide one or more degrees of freedom for the motion of a surgical instrument. While conventional surgical instruments have included effective components to move a surgical instrument in more than one degree of freedom, further improvements can be made with respect to components for actuating surgical instruments and surgical instrument end effectors.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a force transmission mechanism for a surgical instrument comprises a worm drive, a lever arm, and an actuation element. The lever arm may comprise a follower member at a first end of the lever arm. The follower member engages the worm drive and is configured to be driven by the worm drive. The actuation element is connected to a second end of the lever arm opposite the first end of the lever arm. The actuation element is configured to transmit force to actuate an end effector of the surgical instrument. Rotational movement of the worm drive imparts translational movement to the actuation element via the lever arm.

In accordance with at least one exemplary embodiment, a surgical instrument comprises a shaft, an end effector disposed at a distal portion of the shaft, an actuation element extending through the shaft and coupled to the end effector, and a force transmission mechanism disposed at a proximal portion of the shaft. The force transmission mechanism may comprise a worm drive and a lever arm. The lever arm may comprise a follower member at a first end of the lever arm. The follower member engages the worm drive and is configured to be driven by the worm drive. The actuation element is connected to a second end of the lever arm opposite the first end of the lever arm. The actuation element is configured to transmit force to actuate the end effector. Rotational movement of the worm drive imparts translational movement to the actuation element via the lever arm.

In accordance with at least one exemplary embodiment, a method, for actuating an end effector of a surgical instrument via an actuation element extending from a force transmission mechanism to the end effector disposed at a distal end of a shaft of the surgical instrument, comprises rotating a worm drive of the force transmission mechanism. The method further comprises, in response to rotating a worm drive, moving a lever arm of the force transmission mechanism via a follower connected to the lever arm and coupled with the worm drive. The method further comprises transmitting the movement of the lever arm to the actuation element so the actuation element is translated along a linear direction to actuate the end effector.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Figure 1:
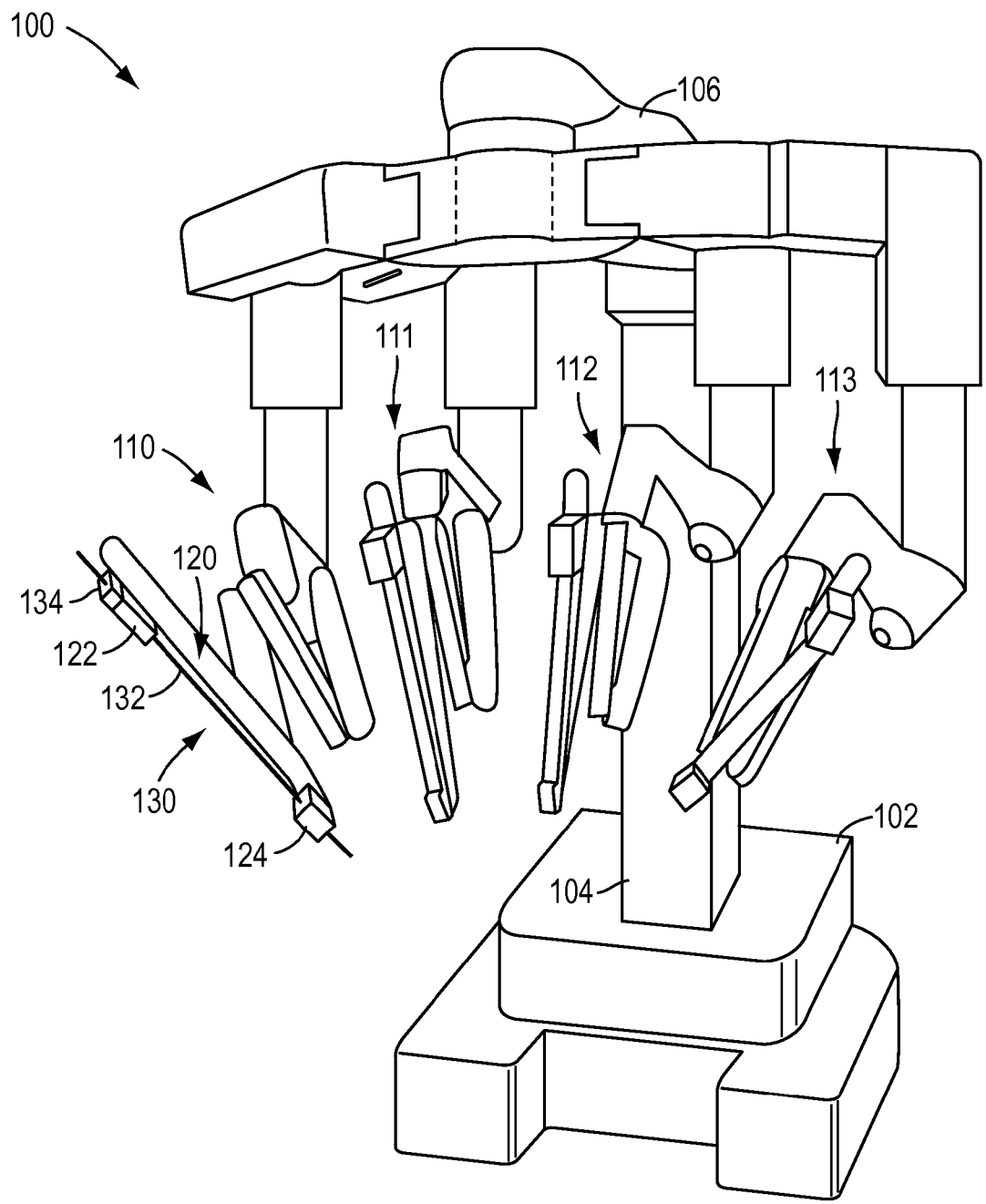
FIG. 1 is a perspective view of a patient side cart of a teleoperated surgical system, according to an exemplary embodiment.

This description and the accompanying drawings that illustrate exemplary embodiments should not be taken as limiting. Various mechanical, compositional, structural, electrical, and operational changes may be made without departing from the scope of this description and claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

In accordance with various exemplary embodiments, the present disclosure contemplates force transmission mechanisms configured to translate rotary motion of a worm drive to translational motion of an actuation element for actuating a surgical instrument in an efficient manner. As a result, space onboard the instrument force transmission mechanism is conserved and manufacturing of the force transmission mechanism is efficient, according to various exemplary embodiments. Moreover, exemplary embodiments of force transmission conversion components can exhibit relatively low friction between contacting parts so that force is efficiently transmitted. Thus, force transmission mechanisms in accordance with various exemplary embodiments efficiently actuate a component of an instrument and provide a high torque to actuate the component.

The various exemplary embodiments described herein contemplate a force transmission mechanism for a surgical instrument that includes a worm drive having a threaded section defining grooves between the threads. A follower member coupled to an end of a lever arm engages the threaded section and be driven by rotational movement of the worm drive, according to an exemplary embodiment. The follower member is, for example, a roller, a ball, a pin, or other follower structure familiar to one of ordinary skill in the art. An actuation element to actuate a component of a surgical instrument is connected to a second end of the lever arm, which may be opposite to the first end of the lever arm, according to an exemplary embodiment. According to an exemplary embodiment, rotational movement of the worm drive is converted to translational movement of the actuation element via the lever arm pivoting relative to the force transmission mechanism. According to another exemplary embodiment, rotational movement of the worm drive is converted to translational movement of the actuation element via the lever arm sliding along a linear direction relative to the force transmission mechanism. The lever arm is coupled to the actuation element via a coupler that transmits force from the lever arm to the actuation element and also permits rolling movement of the actuation element relative to the lever arm, according to an exemplary embodiment. According to another exemplary embodiment, the lever arm includes teeth that engage with the threaded section of a worm drive.

Referring now to FIG. 1, an exemplary embodiment of a patient side cart 100 of a teleoperated surgical system is shown. A teleoperated surgical system may further include a surgeon console (not shown) for receiving input from a user to control instruments mounted at patient side cart 100. A teleoperated surgical system also can include an auxiliary equipment/vision cart (not shown), which may optionally include at least part of the system's computer control equipment, as described in, for example, U.S. Patent Application Pub. No. US 2013/0325033 A1, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety. Further, the exemplary embodiments described herein may be used, for example, with a da Vinci® Surgical System, such as the da Vinci Si® Surgical System, or the da Vinci® Xi™ Surgical System, both with or without Single-Site® single orifice surgery technology, all commercialized by Intuitive Surgical, Inc.

Patient side cart 100 may include a base 102, a main column 104, and a main boom 106 connected to main column 104. Patient side cart 100 may also include a plurality of teleoperated manipulator arms 110, 111, 112, 113, each of which is connected to main boom 106. Manipulator arms 110, 111, 112, 113 each include an instrument mount portion 120 to which an instrument 130 may be mounted, which is illustrated as being attached to manipulator arm 110. Portions of manipulator arms 110, 111, 112, 113 are manipulated during a surgical procedure according to commands provided by a user at the surgeon console. In an exemplary embodiment, signal(s) or input(s) transmitted from a surgeon console are transmitted to the control/vision cart that interprets the input(s) and generate command(s) or output(s) to be transmitted to the patient side cart 100. For example, the command(s)/output(s) are transmitted through drive interface devices and ultimately to the surgical instrument transmission mechanism to cause manipulation of an instrument 130 (only one such instrument being mounted in FIG. 1) and/or portions of manipulator arm 110 to which the instrument 130 is coupled at the patient side cart 100.

Instrument mount portion 120 includes an actuation interface assembly 122 and a cannula mount 124. A shaft 132 of instrument 130 extends through cannula mount 124 (and on to a surgery site during a surgical procedure). A force transmission mechanism 134 of instrument 130 is mechanically coupled with the actuation interface assembly 122, according to an exemplary embodiment. Cannula mount 124 is configured to hold a cannula (not shown in FIG. 1) through which shaft 132 of instrument 130 may extend to a surgery site during a surgical procedure. Actuation interface assembly 122 contains a variety of drive (e.g., input drive) and other mechanisms that are controlled to respond to input commands at the surgeon console and transmit forces to the force transmission mechanism 134 to actuate instrument 130, as those skilled in the art are familiar with, and thus can be broadly classified as a drive interface device. For instance, the input drives of actuation interface assembly 122 may directly engage with an interface structures (not shown) of force transmission mechanism 134 and transmit forces to force transmission mechanism 134, as will be discussed below.

Although the exemplary embodiment of FIG. 1 shows an instrument 130 attached to only manipulator arm 110 for ease of illustration, an instrument may be attached to any and each of manipulator arms 110, 111, 112, 113. An instrument 130 may be a surgical instrument with an end effector or may be an endoscopic imaging instrument or other sensing instrument utilized during a surgical procedure to provide information, (e.g., visualization, electrophysiological activity, pressure, fluid flow, and/or other sensed data) of a remote surgical site. In the exemplary embodiment of FIG. 1, a surgical instrument with an end effector or an imaging instrument may be attached to and used with any of manipulator arms 110, 111, 112, 113. However, the embodiments described herein are not limited to the exemplary embodiment of the patient side cart of FIG. 1 and various other teleoperated surgical system configurations, including patient side cart configurations, may be used with the exemplary embodiments described herein.

Figure 2:
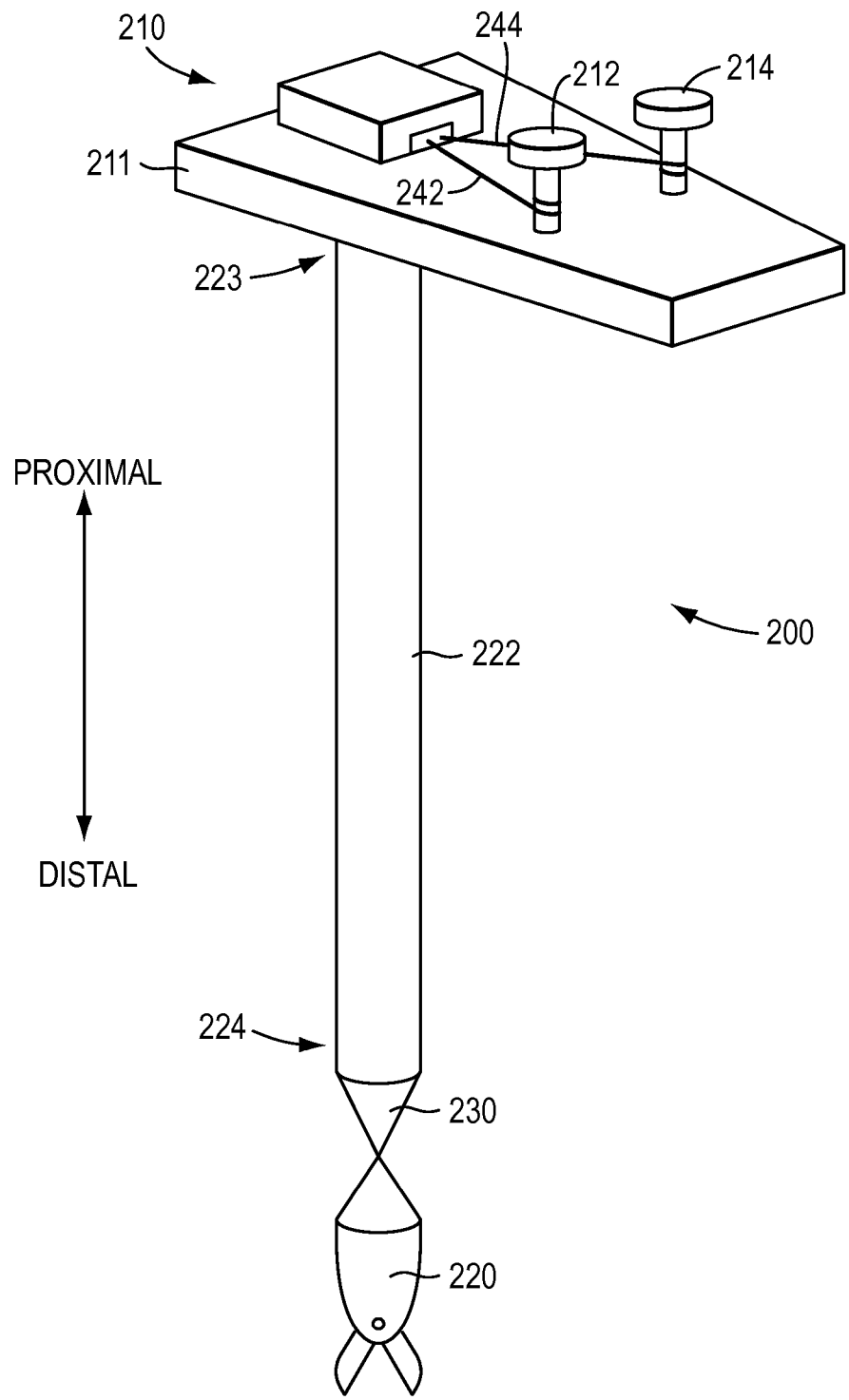
FIG. 2 is a diagrammatic perspective view of a surgical instrument, according to an exemplary embodiment.

Turning to FIG. 2, a schematic perspective view of an exemplary embodiment of a surgical instrument 200 is shown. For instance, surgical instrument 200 may be used as instrument 130 with the patient side cart 100 of the exemplary embodiment of FIG. 1. Surgical instrument 200 includes a force transmission mechanism 210 (a chassis 211 which is shown in the exemplary embodiment of FIG. 2, with a housing being removed from the illustration so as reveal components of the force transmission mechanism 210 within), a shaft 222 connected to force transmission mechanism 210 at a proximal end 223 of shaft 222, an optional wrist 230 connected to a distal end 224 of shaft 222, and an end effector 220 connected to wrist 230 (if any) or directly to the shaft 222 (if no wrist exists). Shaft 222 may be flexible or rigid. Various diameters for shaft 222 may exist in a range suitable for minimally invasive surgery. According to an exemplary embodiment, shaft 222 has a diameter ranging from about 3 mm to about 15 mm. For example, shaft 222 may have a diameter of 3 mm, 5 mm, 8 mm, 13 mm, or 15 mm. According to another exemplary embodiment, the diameter of shaft 222 ranges, for example, from about 5 mm to about 8 mm. End effector 220 may comprise, for example, forceps, a needle driver for suturing, cutting devices, dissecting devices, clip appliers, and other end effector configurations for performing various surgical procedures.

Surgical instrument 200 may include one or more members to transmit force between force transmission mechanism 210 and end effector 220 and/or between force transmission mechanism 210 and wrist 230. For example, actuation elements 242, 244 connect force transmission mechanism 210 to end effector 220 to provide actuation forces to end effector 220, such as by extending through an interior of shaft 222. By utilizing actuation elements 242, 244, force transmission mechanism 210 actuates end effector 220 to control, for example, a jaw of end effector 220 (or other moveable part of end effector 220). In another example, actuation elements 242, 244 are used to actuate wrist 230 in one or more orientation degrees of freedom (e.g. pitch and/or yaw). Actuation elements 242, 244 may be tension members, such as when force transmission mechanism 210 is a pull-pull mechanism, or one or more rods, tubes, or cables, such as when force transmission mechanism 110 is a push-pull mechanism, as described in U.S. Pat. No. 8,545,515 (issued Oct. 1, 2013), which is hereby incorporated by reference in its entirety.

Force transmission mechanism 210 may include one or more components to engage with a patient side cart of a teleoperated surgical system to transmit a force provided by patient side cart to surgical instrument 100. Persons skilled in the art will be familiar with surgical instrument force transmission mechanisms, which receive a mechanical input force from a power source (e.g., an electric motor from a manipulator supporting the instrument) and convert and/or redirect the received force to an output force to drive a component (e.g., a wrist, and end effector) on the instrument. For example, force transmission mechanism 210 may connect with the actuation interface assembly 122 of the patient side cart 100 of the exemplary embodiment of FIG. 1 so actuation interface assembly 122 transmits forces to force transmission mechanism 210 to actuate instrument 200. According to an exemplary embodiment, force transmission mechanism 210 includes one or more driven actuation input mechanisms 212, 214 that engage (e.g., via a distal end of force transmission mechanism 210) with a manipulator of a patient side cart, such as actuation interface assembly 122 of patient side cart 100.

According to an exemplary embodiment, actuation input mechanisms 212, 214 may interact with a manipulator of a patient side cart, such as actuation interface assembly 122 of patient side cart 100, via a sterile adapter (not shown), as will be described below. One exemplary type of actuation input mechanism that can be used in force transmission mechanism 210 is a pull-pull mechanism, exemplary embodiments of which are described in U.S. Pat. No. 8,545,515, which is hereby incorporated by reference in its entirety. According to an exemplary embodiment, force transmission mechanism 210 may utilize a pull-pull mechanism, actuation elements 242, 244 may be tension members, and driven actuation input mechanisms 212, 214 may be capstans that are rotationally driven by actuation interface assembly 122 to tension actuation elements 242, 244 to actuate the instrument. Thus, driven actuation input mechanisms 212, 214 utilize actuation forces from an actuation interface assembly to actuate instrument 200.

Force transmission mechanism 210 may include other components in addition to or in lieu of capstans to actuate various other functionalities of a surgical instrument, as those having ordinary skill in the art are familiar with. Such components include, but art no limited to, gears, clutches, pulleys, linkages, and other mechanisms to convert input force and/or motion into a desired output force and/or motion. Further, force transmission mechanism 210 may include other numbers of actuation input mechanisms 212, 214 than shown in the exemplary embodiment of FIG. 2, such as, for example, one, three, four, five, six, seven, eight or more actuation input mechanisms. For example, any number of actuation input mechanisms 212, 214 may be used, depending on the nature of a surgical instrument and depending upon the degrees of operational freedom of such an instrument.

The force transmission mechanism of FIG. 2 accurately converts rotational movement, such as at actuation input mechanisms 212, 214, into translational movement of an actuation element for actuation of a surgical instrument. However, such force transmission mechanisms require many moving parts and intermeshed elements, increasing manufacturing costs and making maintenance and cleaning more difficult, potentially limiting the number of times such an instrument may be used. It may be desirable to provide a force transmission mechanism that provides for both roll and translational movement of an actuation element, while advantageously using fewer parts and providing a lower manufacturing cost.

Figure 3:
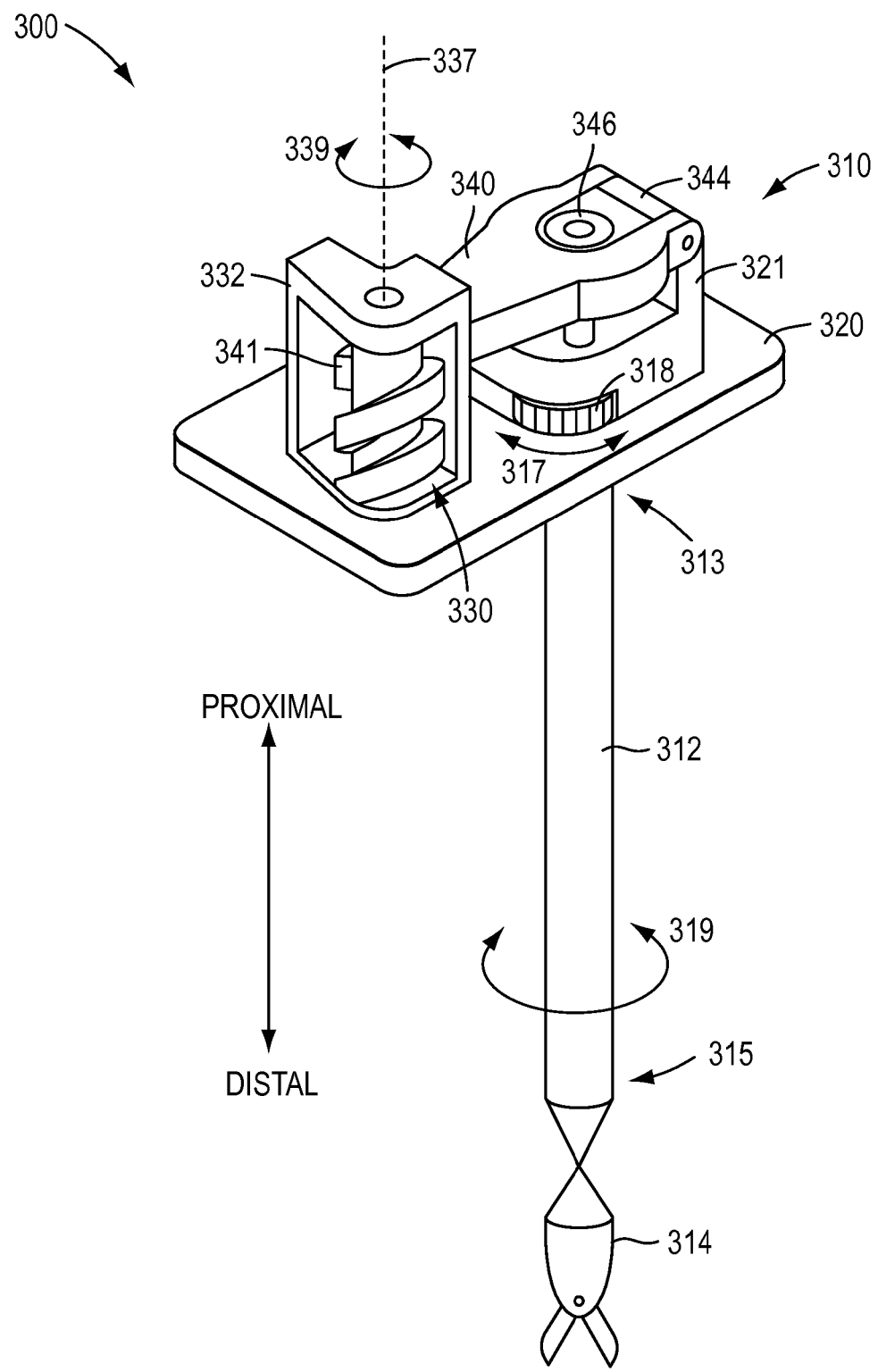
FIG. 3 is a perspective view of a surgical instrument depicting an interior view of a force transmission mechanism, according to an exemplary embodiment.

An exemplary embodiment of a surgical instrument 300 is shown in FIG. 3. Surgical instrument 300 may be used as instrument 130 with the patient side cart 100 of the exemplary embodiment of FIG. 1. Surgical instrument 300 includes a force transmission mechanism 310 (a housing of force transmission mechanism 310 not being shown in FIG. 3 to reveal components of the force transmission mechanism 310 within), a shaft 312 connected to force transmission mechanism 310 at a proximal end 313 of shaft 312, and an end effector 314 connected to a distal end 315 of shaft 312. Surgical instrument 300 may be a non-wristed instrument and may lack a wrist, such as wrist 230 of the exemplary embodiment of FIG. 2, as shown in the exemplary embodiment of FIG. 3. However, the various exemplary embodiments described herein are not limited to non-wristed instruments and may instead include an articulatable wrist mechanism, as described above with regard to the exemplary embodiment of FIG. 2.

Figure 4:
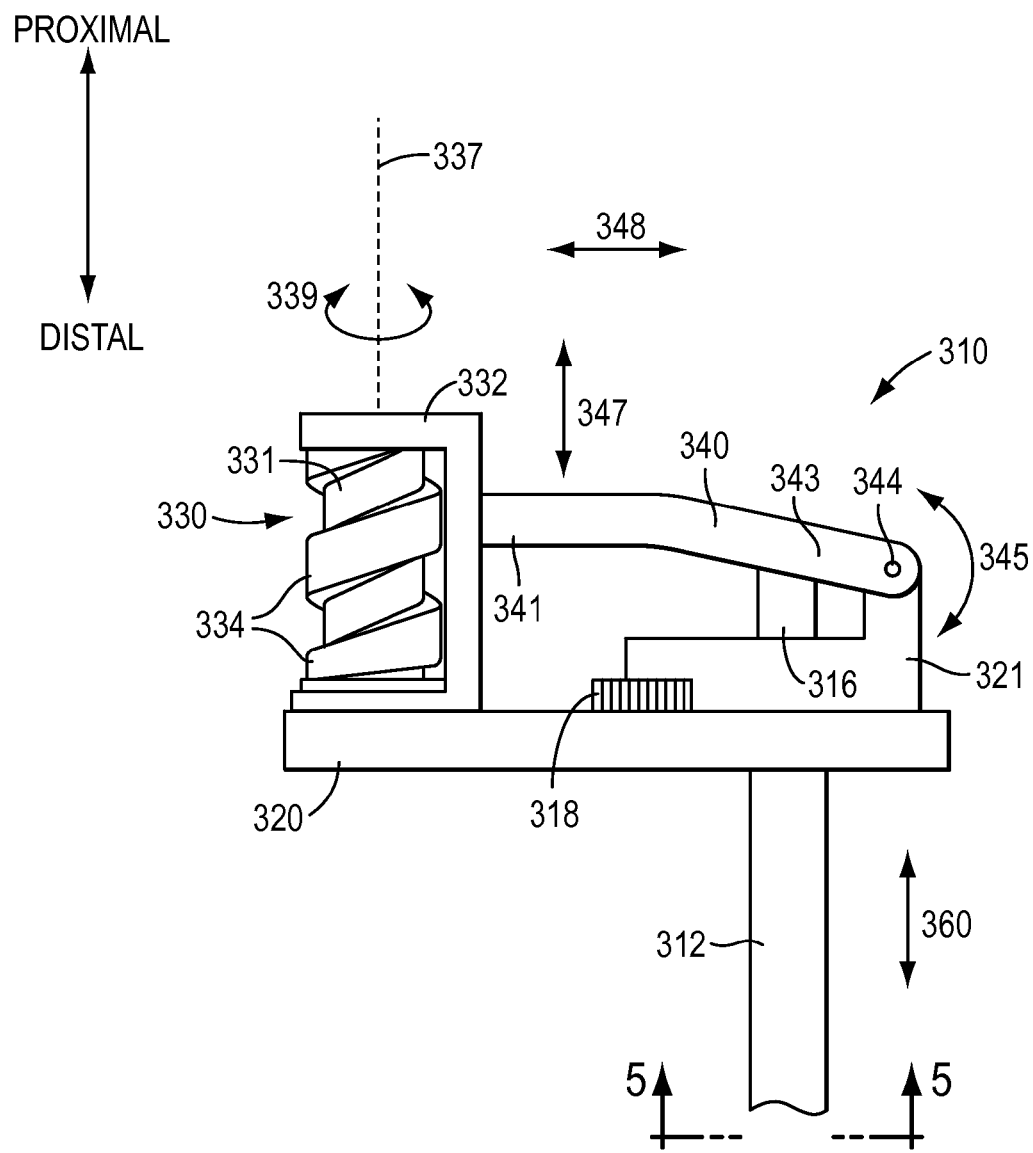
FIG. 4 is a side view of a proximal portion of the surgical instrument of FIG. 3.

Turning to FIG. 4, a proximal portion of surgical instrument 300 is shown from the side. Force transmission mechanism 310 of surgical instrument 300 includes a chassis 320 and a housing (not shown) that connects to chassis 320 to form an enclosure covering the various components supported on chassis 320. Force transmission mechanism 310 further includes an actuation element 316 extending from force transmission mechanism 310 through an interior of shaft 312. According to an exemplary embodiment, actuation element 316 connects to and actuates end effector 314 (shown in FIG. 3). Actuation element 316 may be, for example, a push-pull drive element, such as a rod, that extends from force transmission mechanism 310 through an interior of shaft 312 to end effector 314 along a proximal-distal direction of instrument 300, according to an exemplary embodiment.

Figure 19:
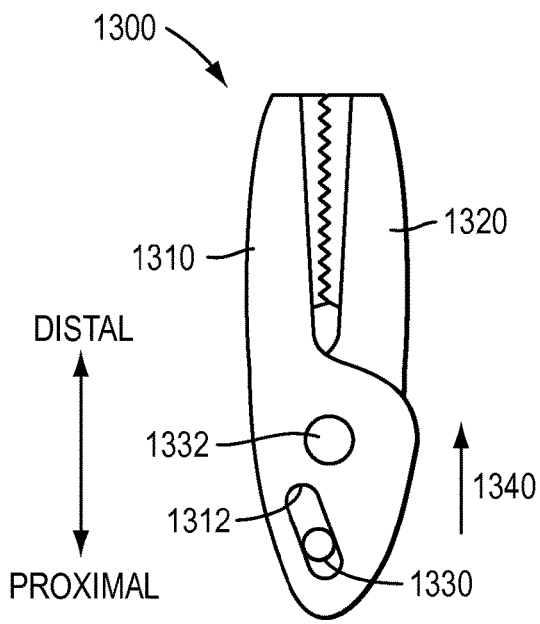
FIG. 19 is a side view of the end effector in a closed position, according to an exemplary embodiment.

End effectors of the various exemplary embodiments described herein can have varying configurations. Turning to FIG. 19, a side view of an end effector 1300 is shown that can be used in the various exemplary embodiments described herein, such as end effector 314 in FIG. 3. In the exemplary embodiment of FIG. 19, end effector 1300 may be, for example, forceps that include jaws 1310, 1320 in a closed state. A projection 1330 disposed at a distal end of an actuation element (not shown) is shown within actuation slot 1312 of jaw 1310. When the actuation element is pushed in direction 1340 in FIG. 19, projection 1330 is forced along direction 1340. Consequently, jaws 1310, 1320 rotate and pivot about pin (not shown) located in connection aperture 1332 along directions 1342 in FIG. 20, causing jaws 1310, 1320 to separate and open. End effector 1300 may be closed by reversing the operation described above, e.g., by pulling the actuation element in a direction opposite to direction 1340 in FIG. 19.

Figure 20:
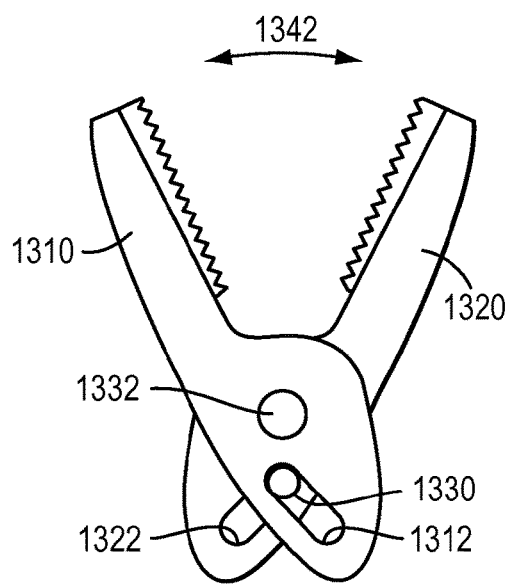
FIG. 20 is a side view of the end effector of FIG. 19 in an open position.
Figure 21:
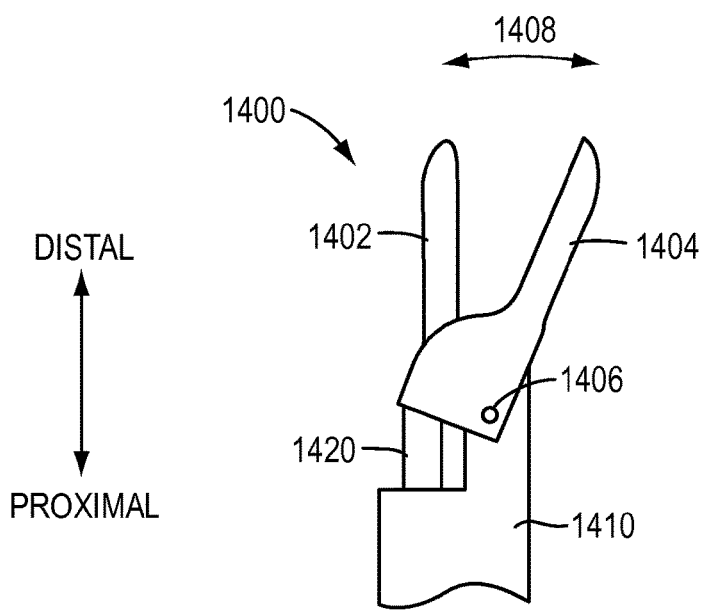
FIG. 21 is a side view of the end effector, according to another exemplary embodiment.

FIG. 21 depicts another exemplary embodiment of an end effector 1400 that can be used in the various exemplary embodiments described herein, such as end effector 314 in FIG. 3. End effector 1400 may be, for example, forceps that include a first non-pivoting jaw 1402 and a pivoting jaw 1404 that pivots about a pin 1406, such as along the directions indicated by arrows 1408 in FIG. 21. An actuation element 1420 extends through a shaft 1410 of a surgical instrument and couple to jaw 1404 to actuate jaw 1404, as depicted in the exemplary embodiment of FIG. 21. According to an exemplary embodiment, end effector 1400 may be an ultrasonic end effector. For example, jaw 1402 may be an ultrasonic blade with pivoting jaw 1404 configured to clamp tissue against jaw 1402. The end effectors of FIGS. 19-21 are non-limiting examples, and end effectors of the various exemplary embodiments described herein may utilize other end effectors familiar to one of ordinary skill in the art.

Force transmission mechanism 310 may include actuation element 316 as the sole actuation element 316 of force transmission mechanism 310 (such as, for example, when instrument 300 is a non-wristed instrument) or force transmission mechanism 310 may include additional actuation elements (not shown), such as one or more actuation element(s) to actuate a wrist, such as wrist 230 of the exemplary embodiment of FIG. 2.

As discussed above with regard to the exemplary embodiment of FIG. 2, force transmission mechanism 310 may include one or more actuation input mechanisms that engage with a manipulator of a patient side cart, such as actuation interface assembly 122 of patient side cart 100 of FIG. 1. For example, force transmission mechanism 310 may directly engage an actuation interface assembly of a manipulator of a patient side cart or force transmission mechanism 310 may engage the actuation interface assembly via a sterile adapter (not shown) located between force transmission mechanism 310 and the actuation interface assembly.

Figure 5:
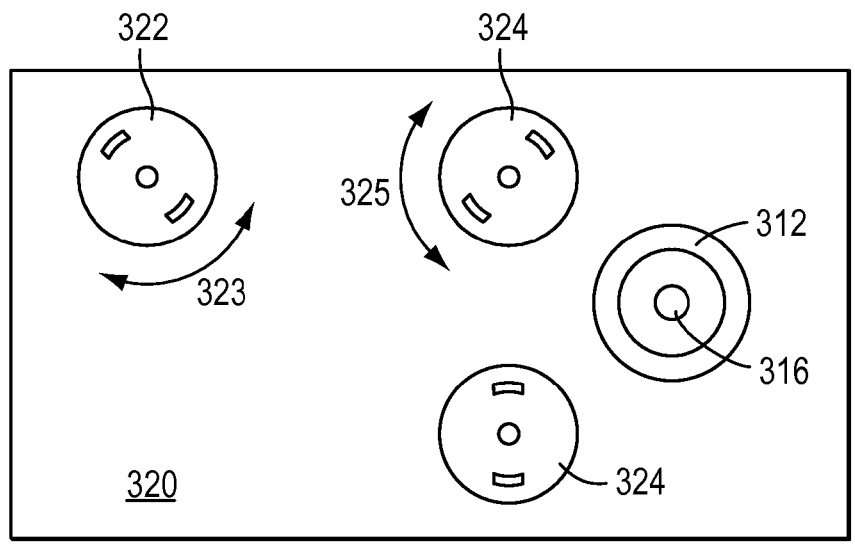
FIG. 5 is a bottom view of the proximal portion of the surgical instrument of FIG. 3, with a cross-sectional view through shaft along line 5-5 of FIG. 4.

By engaging with the actuation interface assembly, force transmission mechanism 310 utilizes actuation forces from the actuation interface assembly (e.g., through servo motors driving shafts that rotate drive disks of the force transmission mechanism 310) to actuate instrument 300, such as to actuate end effector 314 of instrument 300. As shown in FIG. 5, which is a bottom view of force transmission mechanism 310, as well as a cross-sectional view through shaft 312 along line 5-5 of FIG. 4, chassis 320 of force transmission mechanism 310 includes an actuation input mechanism 322 to receive forces from an actuation interface assembly (e.g., directly from an actuation interface assembly or indirectly from an actuation interface assembly via a sterile adapter) and drive actuation element 316, which extends through an interior of shaft 312. For instance, actuation input mechanism 322 may be rotated along the directions indicated by arrows 323 to cause actuation element 316 to be driven into and out of the page of the exemplary embodiment of FIG. 5, as will be discussed below.

Force transmission mechanism 310 may include other actuation interface mechanisms to receive forces from an actuation interface mechanism and drive other components of force transmission mechanism 310. For example, chassis 320 may include one or more actuation interface mechanism(s) 324. An actuation interface mechanism 324 can receive forces from an actuation interface assembly to drive a roll gear 318 connected to the actuation interface mechanism 324. Roll gear 318 is engaged with a distal portion of shaft 312 so that when an actuation interface mechanism 324 is driven by forces from an actuation interface assembly (directly or indirectly via a sterile adapter), such as along the directions indicated by arrows 325 in the exemplary embodiment of FIG. 5, roll gear 318 is rotated along the directions indicated by arrows 317 in FIG. 3, which causes shaft 312 to be rolled, such as along the directions indicated by arrows 319 in FIG. 3. According to an exemplary embodiment, force transmission mechanism 310 includes one or more stops to limit the rotational movement of shaft 312, such as, for example, to limit the rotational movement of shaft 312 to +/−360 degrees or less. According to another exemplary embodiment, force transmission mechanism 310 includes one or more stops to limit the rotational movement of shaft 312, such as, for example, to limit the rotational movement of shaft 312 to +/−320 degrees or less. According to another exemplary embodiment, force transmission mechanism 310 may be configured to roll shaft 312 in a continuous manner without restriction, such as by lacking a stop to limit the rotational movement of shaft 312.

As discussed above with regard to the exemplary embodiment of FIG. 5, force transmission mechanism 310 receives forces from an actuation interface assembly to drive actuation element 316, such as via actuation input mechanism 322. For example, actuation input mechanism 322 may be rotated along the directions indicated by arrows 323 to drive actuation element 316 in and out of the page of FIG. 5. Thus, force transmission mechanism 310 is configured to translate the rotary motion of actuation input mechanism 322 into a translational (e.g., push-pull movement) of actuation element 316 with a high force output. Further, force transmission mechanism 310 may be configured to translate the rotary motion to the translational motion in an efficient manner, such as by using few parts. In this way, space onboard the instrument force transmission mechanism may be conserved and manufacturing may be efficient. Moreover, exemplary embodiments of force transmission conversion components can exhibit relatively low friction between contacting parts so that force is efficiently transmitted. Thus, force transmission mechanisms in accordance with various exemplary embodiments, including force transmission mechanism 310, can efficiently actuate a component of a surgical instrument, such as, for example, end effector 314, and provide a high force to actuate the component.

Figure 6:
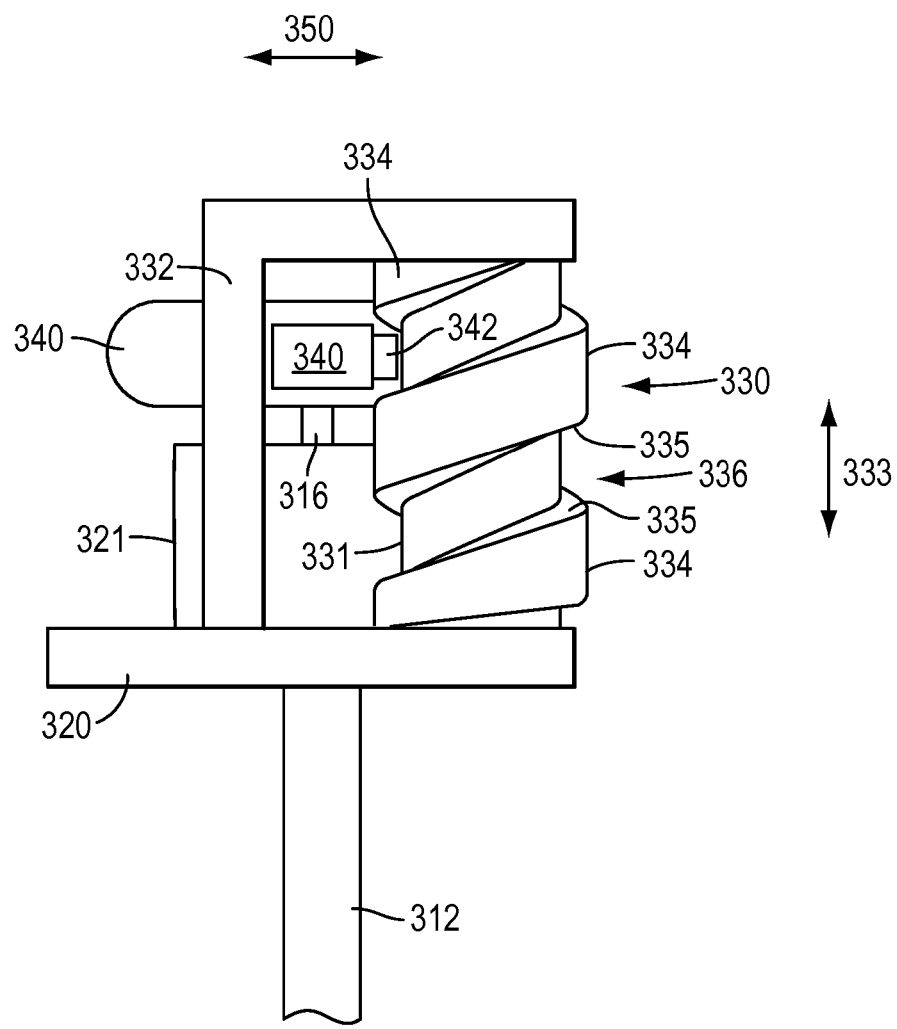
FIG. 6 is an end view of the proximal portion of the surgical instrument of FIG. 3.

According to various exemplary embodiments, force transmission mechanisms utilize a worm drive and follower lever assembly to convert rotational motion to translational motion. With reference to the exemplary embodiments of FIGS. 3-7, for example, force transmission mechanism 310 can include a worm drive 330 connected to and extending generally perpendicular to the plane of chassis 320. A mount 332 holds and supports worm drive 330 relative to the chassis 320, as shown in FIGS. 3, 4, and 6. Worm drive 330 is coupled to actuation input mechanism 322. Accordingly, rotation of actuation input mechanism 322, such as along the direction of arrows 323 in FIG. 5, imparts rotation to worm drive 330 about an axis 337, such as along the directions indicated by arrows 339 in the exemplary embodiment of FIGS. 3, 4, and 7. According to an exemplary embodiment, worm drive 330 is mounted to chassis 320 and mount 332 so that worm drive 330 rotates relative to chassis 320 and mount 332. Thus, worm drive 330 is configured to rotate about axis 337 in the directions of arrows 339 relative to chassis 320 and mount 332.

According to an exemplary embodiment, worm drive 330 includes a helically wrapped threaded section 334 that spirals along a longitudinal length of a shaft 331, as shown in FIGS. 4 and 6. Threaded section 334 may continuously spiral about worm drive 330 one complete turn (e.g., 360 degrees) or more along a longitudinal direction of worm drive 330, according to an exemplary embodiment. According to another exemplary embodiment, threaded section 334 may continuously spiral about worm drive 330 more than one complete turn (e.g., more than 360 degrees) along a longitudinal direction of worm drive 330. For example, threaded section 334 may continuously spiral about worm drive 330 about two turns or more (e.g., about 720 degrees or more), along a longitudinal direction of worm drive 330.

Grooves 336 located between the threads of threaded section 334 provide a space to receive a part of another member driven by worm drive 330, as will be described in more detail below. Thus, shaft 331 has a smaller radial outer diameter than the threads of the threaded section 334, and the opposing surfaces of adjacent threads define axial surfaces 335 that together with the surface of shaft 331 define the grooves 336. According to an exemplary embodiment, grooves 336 is a single, continuous groove that spirals along worm drive 330.

As mentioned above, force transmission mechanism 310 can include a connecting member that engages and is driven by the worm drive 330. According to an exemplary embodiment, force transmission mechanism 310 includes a lever arm 340 coupled with the worm drive 330. As depicted, lever arm 340 is a class 2 lever, in which the fulcrum is located at one end, input force (effort) is applied at the opposite end, and the output force (resistance) is between the fulcrum and the input force. For example, a first end 341 of lever 340 may be coupled with the worm drive 330, as shown in the exemplary embodiment of FIGS. 3, 4, 6, and 7. According to an exemplary embodiment, first end 341 of lever 340 may be disposed within mount 332, as shown in FIGS. 3 and 6. For example, a pin 352 located at an end of worm drive 330 may be held within mount 332, with rotational axis 337 of worm drive 330 extending through pin 352, as shown in the exemplary embodiment of FIG. 3. Thus, lateral movement of first end 341 relative to worm drive 330, such as along the directions indicated by arrows 350 in FIG. 6, is minimized or prevented by gear mount 332 and the engagement between first end 341 and worm drive 330.

According to an exemplary embodiment, lever 340 is coupled with a gear section of worm drive 330 via a follower. As shown in the exemplary embodiment of FIG. 6, a follower 342 is connected to first end 341 of lever 340, with follower 342 engaged with the gear section of worm drive 330. For example, follower 342 may be disposed within groove 336 between portions of threaded section 334. In this way, follower 342 engages with axial surfaces 335 of threaded section 334 and/or central section 331 of worm drive 330. As worm drive 330 is rotated, such as via rotation of actuation input mechanism 322, follower 342 is driven upward or downward relative to chassis 320, such as along the directions indicated by arrows 333 in the exemplary embodiment of FIG. 6. As a result, lever 340 is driven by the rotation of worm drive 330 and is also moved relative to chassis 320. For instance, first end 341 of lever 340 may move in a generally linear manner along the directions indicated by arrows 333 in FIG. 6. Due to relatively low friction between follower 342 and worm drive 330, the transmission of forces between worm drive 330 and lever 340 is efficient and force transmission mechanism 310 may provide a relatively large force to actuate instrument 300, such as to actuate end effector 314. Further, low friction between lever 340 and worm drive 330 may permit surgical instrument 300 to be back-drivable. For example, if end effector 314 is in an actuated configuration (e.g., end effector is in an open position), the end effector 314 may be back-driven to a non-actuated configuration (e.g., closed position of an end effector). In another example, a force transmission mechanism of the various exemplary embodiments described herein may be used to actuate a wrist, which is back-drivable. Thus, when the wrist is in a bent configuration, for example, the wrist may be back-driven to a non-actuated configuration (e.g., a straight configuration). Back-driving may occur, for example, as the instrument is withdrawn from a cannula due to contact between the cannula and end effector 314 and/or wrist. As a result, damage to instrument 300 and/or the cannula may be minimized or avoided.

Figure 8:
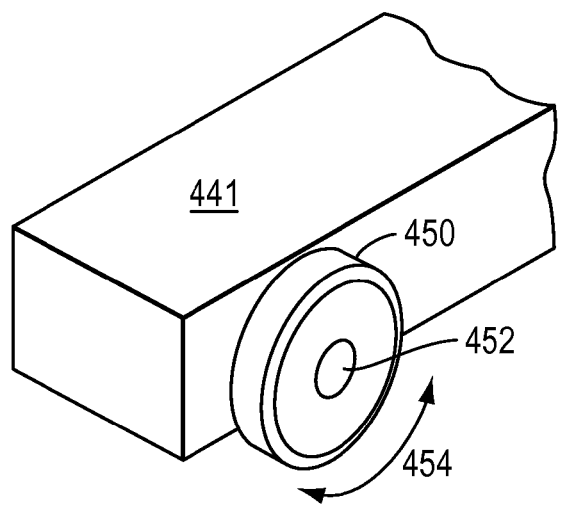
FIG. 8 is a perspective view of an end of a lever comprising a follower, according to an exemplary embodiment.

The follower of a force transmission mechanism can have various designs. Turning to FIG. 8, first end 441 of a lever (e.g., lever 340) is shown that includes a follower 450 configured to move relative to first end 441, according to an exemplary embodiment. Follower 450 is a roller connected to first end 441, such as via a shaft 452, so that follower 450 may rotate relative to first end 441, such as along the directions indicated by arrows 454 in the exemplary embodiment of FIG. 8. Thus, follower 450 engages with one or more surfaces of the worm drive, such as axial surfaces 335 of threaded section 334 and/or central section 331 of worm drive 330, so that follower 450 is rotated relative to first end 441 as the worm drive is rotated. As a result, a low friction connection may be provided between first end 441 and the worm drive.

A follower of a force transmission mechanism need not be movably coupled relative to a lever of the force transmission mechanism. As shown in the exemplary embodiment of FIG. 9, a follower 550 is a ball fixedly connected to a first end 541 of a lever (e.g., lever 340), such as via a shaft 552 or directly connected. Follower 550 may engage a threaded section of a worm drive, such as by disposing follower 550 with grooves 336 of worm drive 330, as discussed above with regard to the exemplary embodiment of FIG. 6. The ball may be, for example, a plastic ball or a metal ball (e.g., a stainless steel ball). As the worm drive is rotated, follower 550 slides along surfaces of the worm drive, such as axial surfaces 335 of threaded section 334 and/or central section 331 of worm drive 330, to move first end 541 via rotation of the worm drive. Although follower 550 does not move relative to first end 541, there is little friction between follower 550 and worm drive 330. As a result, forces may be efficiently transmitted between the helical gar and first end 541.

Figure 9:
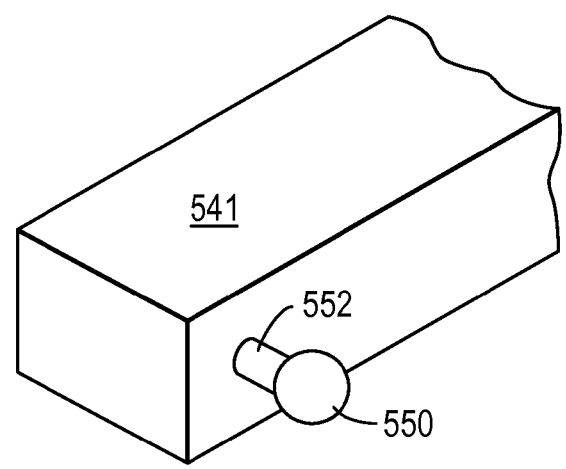
FIG. 9 is a perspective view of an end of a lever comprising a follower, according to another exemplary embodiment.
Figure 10:
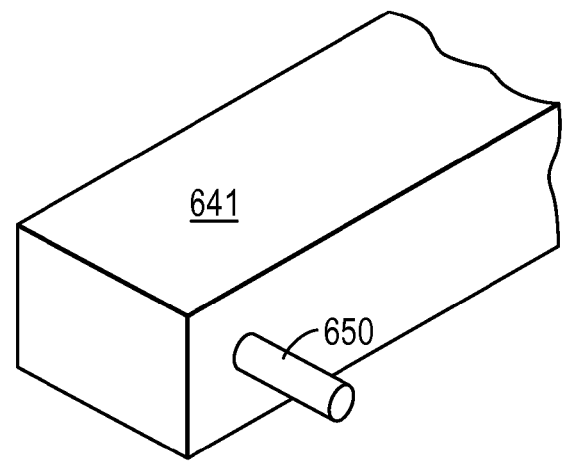
FIG. 10 is a perspective view of an end of a lever comprising a follower, according to another exemplary embodiment.

Turning to FIG. 10, an exemplary embodiment of a first end 641 of a lever (e.g., lever 340) is depicted that includes another exemplary follower 650. Follower 650 is a pin fixedly connected to first end 641. Follower 650 may slide along surfaces of a worm drive, such as axial surfaces 335 of threaded section 334 and/or central section 331 of worm drive 330, as the worm drive is rotated, similar to the exemplary embodiment of FIG. 9. According to an exemplary embodiment, follower 650 may be a separate piece joined to first end 641. According to another exemplary embodiment, a lever may be directly coupled with a gear section of worm drive. For instance, follower 650 may have a single-piece (i.e., monolithic) construction with first end 641, so that first end 641 may directly engage the gear section of a worm drive.

The exemplary embodiments of FIGS. 8-10 are non-limiting exemplary embodiments and other configurations for a follower to be received in recess of a worm drive to ride along the surfaces of worm drive threads are contemplated as being with the scope of the present disclosure.

Figure 11:
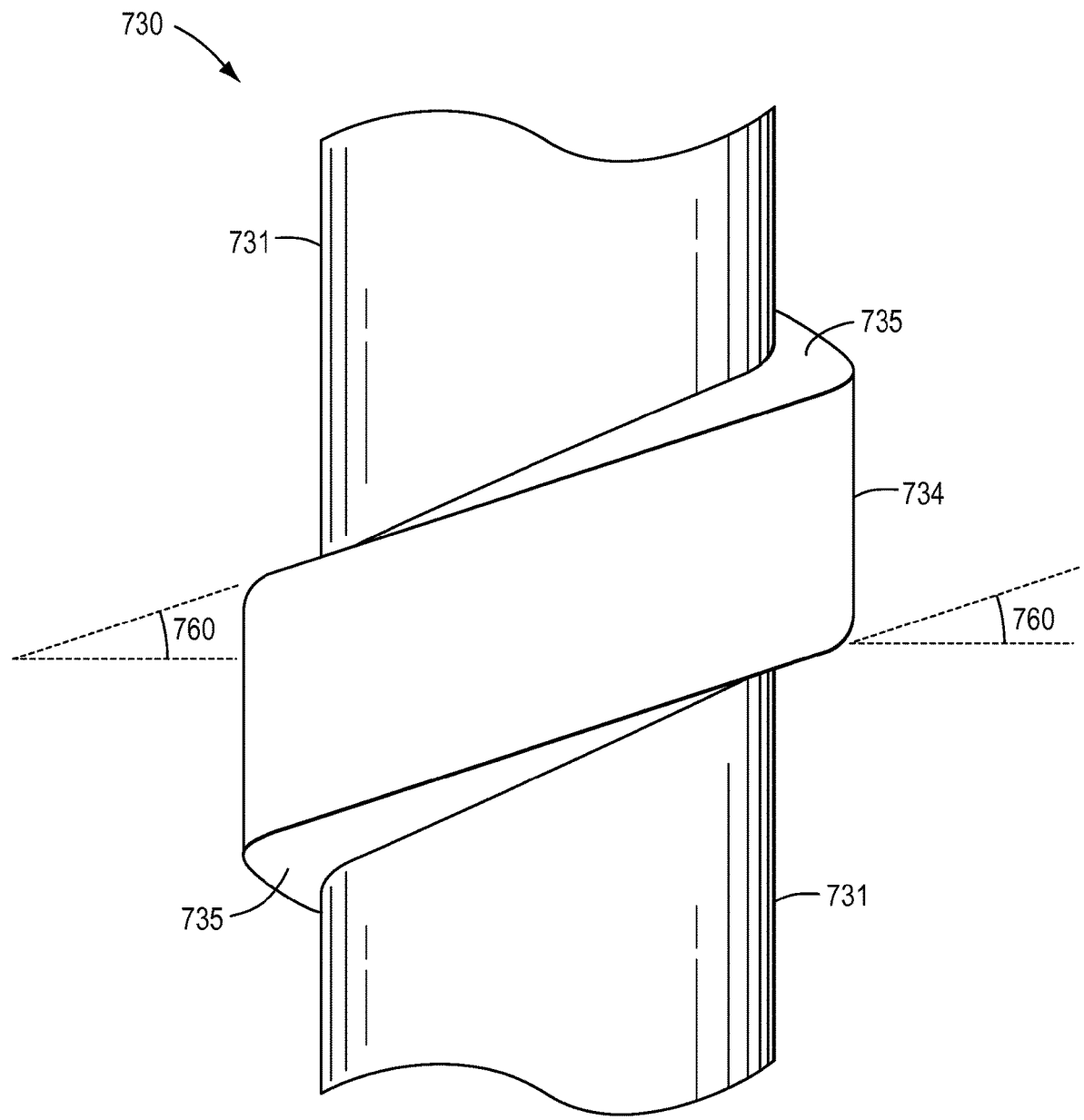
FIG. 11 is a side view of a portion of a worm drive, according to an exemplary embodiment.

A worm drive may be structured to efficiently transmit forces to a lever of a force transmission mechanism and drive the lever as the worm drive is rotated. Turning to FIG. 11, an exemplary embodiment of a worm drive 730 is shown, which may be used in the force transmission mechanisms of the various exemplary embodiments described herein, such as force transmission mechanism 310 of the exemplary embodiment of FIGS. 3-7. Worm drive 730 includes a central section 731 and a threaded section 734 having axial surfaces 735, as described above with regard to the exemplary embodiment of FIGS. 3-7. The slope of axial surfaces 735 of threaded section 734 can be selected to drive a follower of a lever that is engaged with the gear section of worm drive 730, such as with axial surfaces 735 and/or central section 731. According to an exemplary embodiment, axial surfaces 735 may be sloped at an angle 760 of, for example, about 10 degrees to about 60 degrees (e.g., relative to a direction transverse to a longitudinal axis of worm drive 730) to enable a high mechanical advantage and high output force for a force transmission mechanism including worm drive 730, and while permitting an end effector actuated by the force transmission mechanism to be back-drivable. For example, axial surfaces 735 may be sloped at an angle 760 of, for example, about 10 degrees to about 30 degrees, for example about 20 degrees.

Lever 340 may be mounted to chassis 320 so that lever 340 is driven by worm drive 330 to move relative to chassis 320. According to an exemplary embodiment, a second end 343 of lever 340 is mounted to chassis 320 of force transmission mechanism 310. For example, second end 343 of lever 340 is mounted to a mount portion 321 of chassis 321 via a pin 344, as shown in the exemplary embodiment of FIGS. 3, 4, and 7. This arrangement permits lever 340 to pivot relative to mount portion 321, such as along the directions indicated by arrows 345 in the exemplary embodiment of FIG. 4. Thus, as worm drive 330 rotates, such as due to rotation of actuation input mechanism 322, lever 340 is moved as well, due to coupling of lever 340 with worm drive 330. For instance, as worm drive 330 is rotated about axis 337 in the directions indicated by arrows 339, lever 340 pivots about pin 344 relative to chassis 320 in the directions indicated by arrows 345 in the exemplary embodiment of FIG. 4.

By pivotably mounting lever 340 to chassis 320, first end 341 of lever 340 follows a generally arcuate path that is centered at pin 344. According to an exemplary embodiment, the curvature of the arcuate path may be sufficiently large so that the motion of lever 340, such as at first end 341, is a generally linear motion along the directions indicated by arrows 347 in the exemplary embodiment of FIG. 4, although some de minimus motion of first end 341 along the directions indicated by arrows 348 in FIG. 4 could occur due to the arcuate motion of first end 341. As indicated by arrows 360 in FIG. 4, the movement of actuation element 316 in turn also is a generally linear movement, such as along a longitudinal direction of shaft 312. Thus, force transmission mechanism 310, including worm drive 330 and lever 340, may function to translate a rotational movement of worm drive 330 into a linear movement of actuation element 316. As a result, surgical instrument 300, such as end effector 314 (e.g., end effectors of FIGS. 19-21), can be efficiently actuated by force transmission mechanism 310 with low friction and a substantial torque. According to an exemplary embodiment, the motion of first end 341 of lever 340 along a generally arcuate path may cause a change in contact between first end 341 (e.g., follower 342) and worm drive 330 during movement of lever 340 along the generally arcuate path. However, lever 340 and worm drive 330 may be configured to maintain contact with one another as first end 341 moves along the generally arcuate path and contact between first end 341 (e.g., follower 342) and worm drive 330 changes, according to an exemplary embodiment. To facilitate the generally linear movement of first end 341 of lever, worm drive 330 and pin 344 can be located at opposite ends of chassis 320, as depicted in the exemplary embodiment of FIG. 4.

Figure 7:
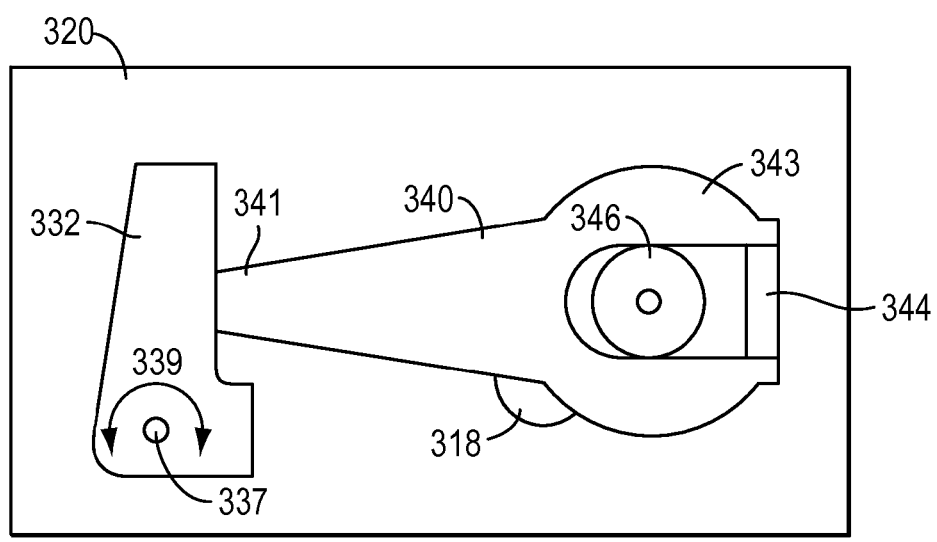
FIG. 7 is a top view of the proximal portion of the surgical instrument of FIG. 3.

Lever 340 may be coupled to actuation member 316 so that actuation member 316 may be actuated via movement of lever 340 and worm drive 330. According to an exemplary embodiment, second end 343 of lever 340 is coupled to actuation element 316 via a coupler 346, as shown in FIGS. 3 and 7. Coupler 346 may be directly connected to second end 343 of lever 340 and directly connected to actuation element 316 so that motion of lever 340 is translated to actuation element 316. For instance, when second end 343 is pivoted about pin 344 along directions 345 in FIG. 4, coupler 346 and actuation element 316 moves along a substantially linear direction indicated by arrows 360 in FIG. 4, such as substantially along the longitudinal direction along shaft 312 of instrument 300. Thus, rotational movement of worm drive 330 can be efficiently translated into the linear movement of actuation element 316, such as via lever 340 and coupler 346. As a result, rotational movement of worm drive 330 can be utilized to drive actuation element 316 along a substantially linear direction, which actuates surgical instrument 300. For instance, actuation element 316 may be a push/pull drive element rod that, when moved in a proximal-distal direction along shaft 312, actuates end effector 314 of instrument 300, such as by opening and closing end effector 314 when end effector 314 comprises a jawed end effector configured to grasp and/or clamp.

Figure 12:
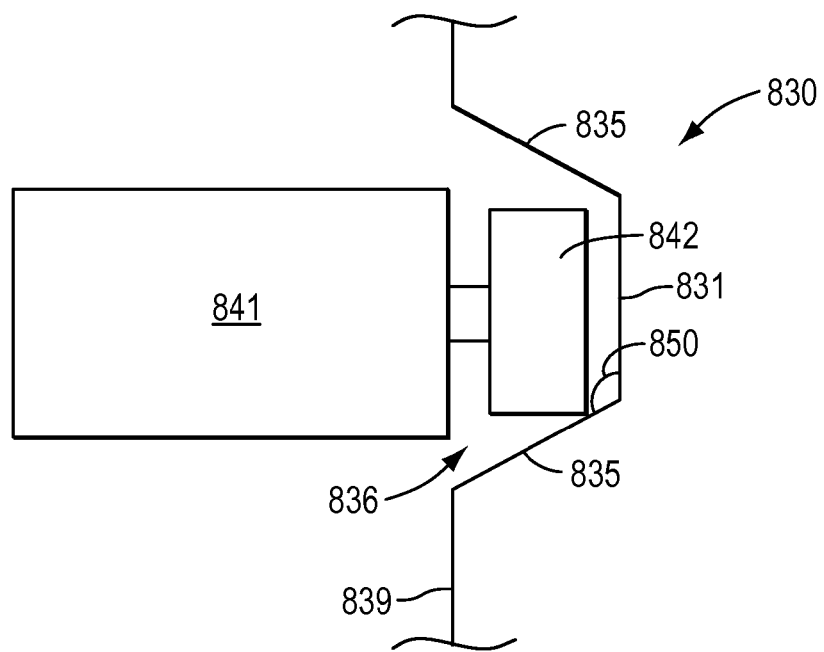
FIG. 12 is a side view of a portion of a worm drive and a follower engaged with the worm drive, according to an exemplary embodiment.

A shape of a gear section of a worm drive may be configured to resist uncoupling a lever from the gear section of the worm drive. Turning to FIG. 12, a cross-sectional view is shown of a first end 841 of a lever that is coupled with a worm drive portion 830 (such as lever 340 and worm drive 330 of FIGS. 3-6), according to an exemplary embodiment. Worm drive portion 830 may be configured according to the exemplary embodiment of FIGS. 3-7 and include grooves 836 between thread surfaces. For example, grooves are defined by a central section 831 and axial surfaces 835. First end 841 may be coupled to worm drive portion 830 via, for example a follower 842 disposed within a groove 836. Follower 842 may be configured according to the various exemplary embodiments described herein, such as the exemplary embodiments of FIGS. 8-10. As shown in the exemplary embodiment, axial surfaces 850 may define an obtuse angle 850 with central section 831, so that grooves 836 are wider at outer radial surface 839 than at central section 831.

Figure 13:
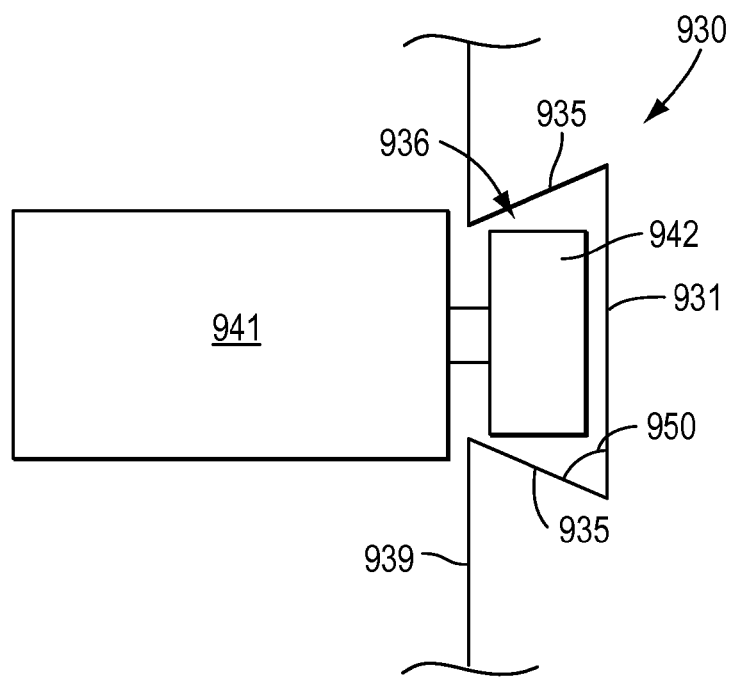
FIG. 13 is a side view of a portion of a worm drive and a follower engaged with the worm drive, according to an exemplary embodiment.

Turning to FIG. 13, a cross-sectional view is shown of a first end 941 of a lever that is coupled with a worm drive portion 930 via a follower 942, according to an exemplary embodiment. Follower 942 may be configured according to the various exemplary embodiments described herein, such as the exemplary embodiments of FIGS. 8-10. Worm drive portion 930 may be configured according to the exemplary embodiment of FIGS. 3-7 and include a groove 936 defined by a central section 931 and axial surfaces 935. As shown in the exemplary embodiment, axial surfaces 950 may define an acute angle 950 with central section 931, so that groove 936 is wider at central section 931 than at an outer radial surface 939. As a result, follower 942 may be more easily retained within groove 936 and worm drive portion 930 and lever first end 941 may resist decoupling from one another.

Figure 14:
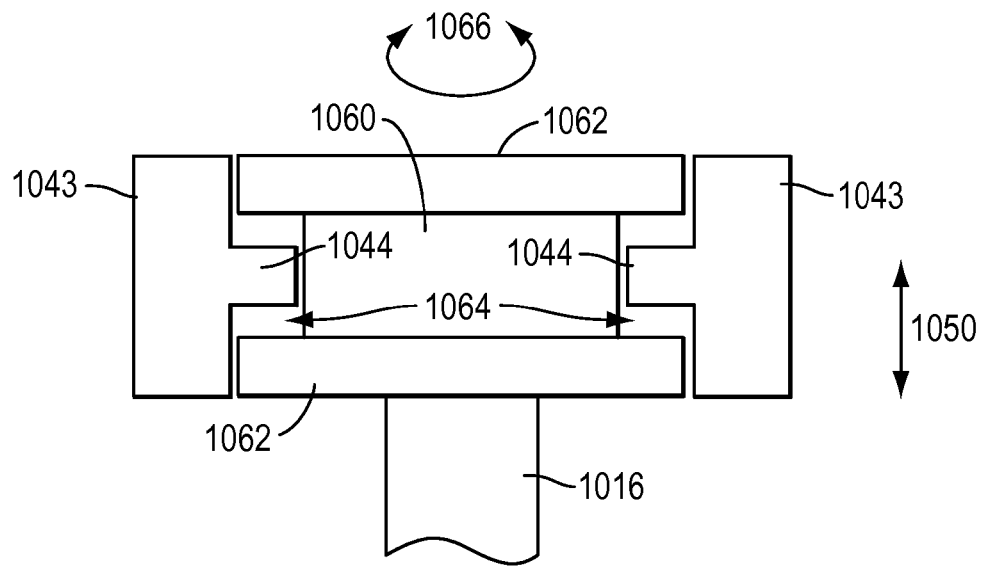
FIG. 14 is a view of a lever coupled to an actuation element, according to an exemplary embodiment.

A lever may be connected to coupler via various structures that translate motion of the lever to an actuation element, while also permitting the actuation element to roll (i.e., rotate about its own axis), such as when a shaft is rotated by a roll gear. Turning to FIG. 14, a side view is shown of a second end 1043 of a lever connected to a coupler 1060, which is in turn fastened to an actuation element 1016. According to an exemplary embodiment, second lever end 1043 may be second lever end 343 and coupler 1060 may be used as coupler 346 in the exemplary embodiment of FIG. 7. The lever, coupler 1060, and actuation element 1016 may be used, for example, in the exemplary embodiment of FIGS. 3-13. Coupler 1060 includes flanges 1062 that define a depression 1064 between flanges 1062. Depression 1064 may be an annular depression, such as when coupler 1060 has a generally circular shape, with FIG. 14 looking upon an edge of the circular shape. Second end 1043 of lever includes projections 1044 disposed within depression 1064 to connect second end 1043 to coupler 1060. Further, coupler 1060 is configured to rotate relative to second end 1043 of the lever (e.g., coupler 1060 rotates relative to projections 1044), such as along the direction indicated by arrows 1066 in the exemplary embodiment of FIG. 14. For instance, when a shaft of an instrument including actuation element 1016 is rolled, such as shaft 312 of the exemplary embodiment of FIG. 4, actuation element 1016 in turn rotates in directions 1066. Thus, second end 1043 and coupler 1060 may permit the lever including second end 1043 to be coupled to coupler 1060 and to actuation element 1016, such as to translate forces from a worm drive to actuation element 1016, while also permitting rotation of actuation element 1016, such as when a shaft including actuation element 1016 is rolled.

When a lever including second end 1043 is moved along the direction indicated by arrows 1050 in FIG. 14, projections 1044 may bear against flanges 1062 to cause coupler 1060 to move. As a result, when the lever including second end 1043 is moved upward or downward along the directions indicated by arrows 1050 (e.g., similar to movement of lever 340 along the direction indicated by arrows 347 in the exemplary embodiment of FIG. 4) and applies force along directions 1050, coupler 1060 is also moved along the direction indicated by arrows 1050 due to the connection between second end 1043 and coupler 1060. In turn, actuation element 1016 also is moved along the directions indicated by arrows 1050 due to the connection between coupler 1060 and actuation element 1016. The various exemplary embodiments described herein are not limited to a connection between a lever and an actuation element, as described above with regard to the exemplary embodiment of FIG. 14, but may use other structures and configurations to connection a lever and actuation element.

Figure 15:
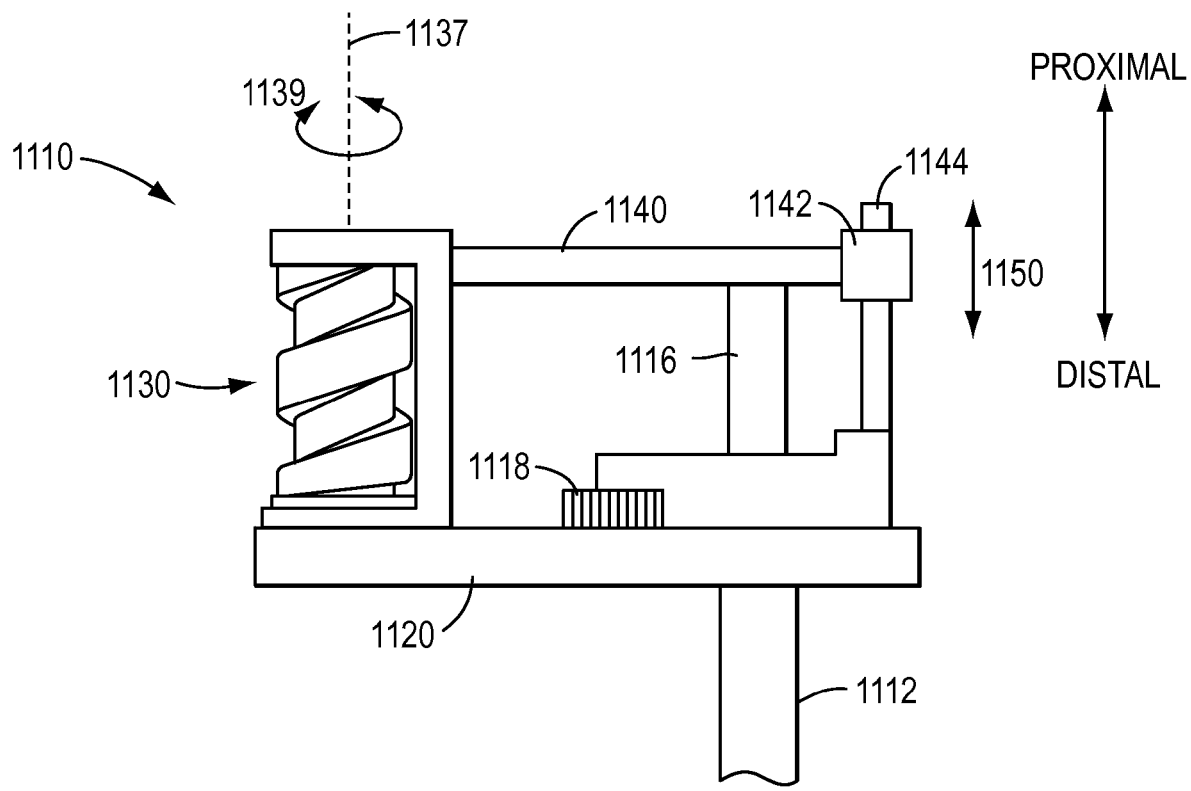
FIG. 15 is a side view of a proximal portion of a surgical instrument with a housing of the force transmission mechanism of the surgical instrument removed, according to an exemplary embodiment.

The various exemplary embodiments described herein are not limited to a lever connecting a worm drive and an actuation element. Turning to FIG. 15, a proximal portion of a surgical instrument is depicted. The surgical instrument may be used as instrument 130 with the patient side cart 100 of the exemplary embodiment of FIG. 1. The surgical instrument includes a force transmission mechanism 1110 (a housing of force transmission mechanism 1110 not being shown in FIG. 15 to reveal components of the force transmission mechanism 1110 within), a shaft 1112 connected to force transmission mechanism 1110, and an end effector (not shown) connected to a distal end of shaft 1112, similar to the exemplary embodiment of FIGS. 3-7. Force transmission mechanism 1110 includes a chassis 1120, a worm drive 1130, and a roll gear 1118, which may be configured according to the exemplary embodiments of FIGS. 3-7 and 11-13.

Force transmission mechanism 1110 can further include a link 1140, which serves as a connecting member coupled to worm drive 1130 and actuation element 1116. Link 1140 may be coupled to worm drive 1130 according to the exemplary embodiments of FIGS. 3-13 described above. Link 1140 may further be coupled to chassis 1120 so that link 1140 moves along a generally linear direction (e.g., proximal-distal direction). According to an exemplary embodiment, link 1140 may be coupled to a post 1144 connected to chassis 1120, such as via a coupler 1142 coupled to post 1144, so that link 1140 may slide up and down post 1144, such along the generally linear direction indicated by arrows 1150 in the exemplary embodiment of FIG. 15. Thus, link 1140, for example, may not be pivotable but instead utilize linear movements. As result, when worm drive 1130 is rotated, such as along the directions indicated by arrows 1139 about axis 1137, link 1140 is moved upward or downward (e.g., along a proximal-distal direction) along post 1144. Due to its coupling to link 1140, actuation element 1116 also is moved back and forth in a linear direction along the directions indicated by arrows 1150 to actuate the surgical instrument. According to an exemplary embodiment, actuation element 1116 may be coupled to link 1140 via a coupler permitting rotation of actuation element 1116 relative to link 1140, such as when a shaft of the instrument including actuation element 1116 is rolled. Other structures may be used to couple to a worm drive and to an actuation element so rotational movement of the worm drive may be translated as linear movement to the actuation element and actuated a surgical instrument.

Figure 16:
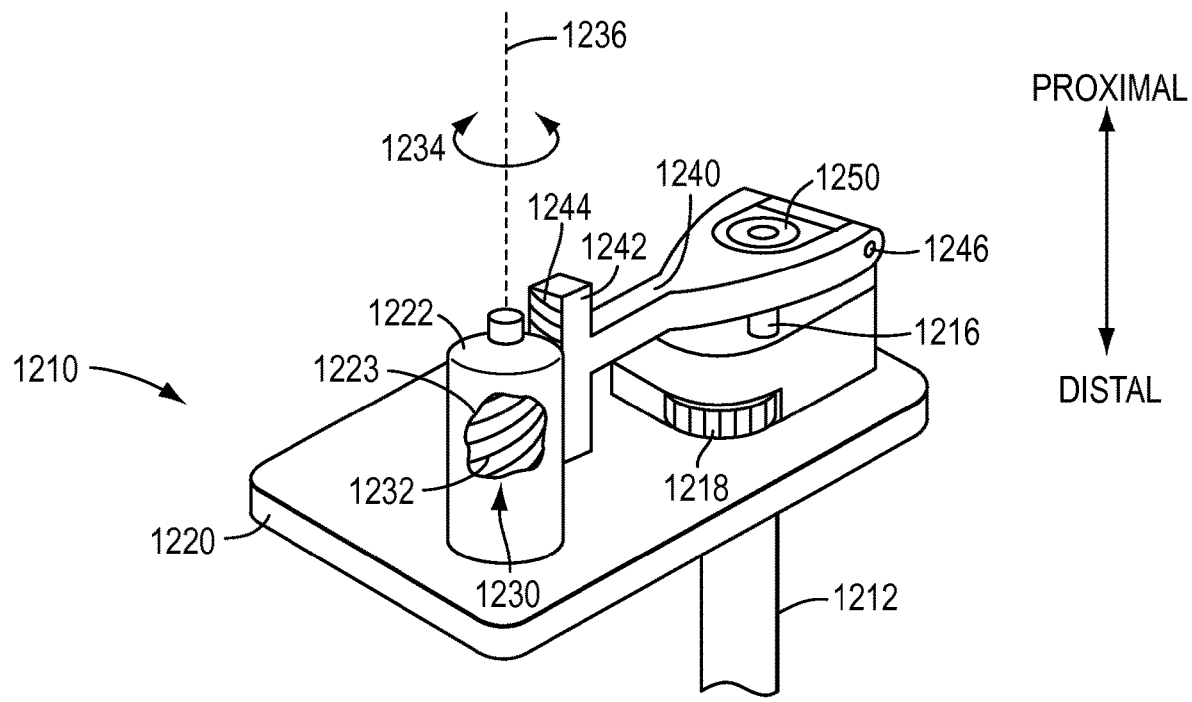
FIG. 16 is a perspective view of a surgical instrument depicting an interior view of a force transmission mechanism, according to an exemplary embodiment.

The various exemplary embodiments described herein may utilize other worm drives and levers than those depicted in the exemplary embodiments of FIGS. 3-14. Turning to FIG. 16, a proximal portion of a surgical instrument is depicted. The surgical instrument may be used as instrument 130 with the patient side cart 100 of the exemplary embodiment of FIG. 1. The surgical instrument includes a force transmission mechanism 1210 (a housing of force transmission mechanism 1210 not being shown in FIG. 16 to reveal components of the force transmission mechanism 1210 within), a shaft 1212 connected to force transmission mechanism 1210, and an end effector (not shown) connected to a distal end of shaft 1212, similar to the exemplary embodiment of FIGS. 3-7. Force transmission mechanism 1210 includes a chassis 1220 including a gear housing 1222 in which a worm drive 1230 is located, as shown via the cutout 1223 of housing 1222 to reveal worm drive 1230 within. Chassis 1220 may further can include a roll gear 1218 and an actuation element 1216 that extends through shaft 1212, which may be configured according to the exemplary embodiment of FIGS. 3-7.

Worm drive 1230 may comprise one or more gear teeth 1232 that spiral about worm drive along a proximal-distal direction of worm drive 1230. For example, gear teeth 1232 may continuously spiral about worm drive 1230 one complete turn (e.g., 360 degrees) or more along a proximal-distal direction of worm drive 1230, according to an exemplary embodiment. According to another exemplary embodiment, gear teeth 1232 may continuously spiral about worm drive 1230 more than one complete turn (e.g., more than 360 degrees) along a proximal-distal direction of worm drive 1230. For example, gear teeth 1232 may continuously spiral about worm drive 1230 about two turns or more (e.g., about 720 degrees or more), along a proximal-distal direction of worm drive 1230.

Force transmission mechanism 1210 may further comprise a lever 1240, which serves as a connecting member coupled to worm drive 1230 and actuation element 1216. Lever 1240 may be coupled to worm drive 1230 by engaging head 1242 of lever 1240 with gear teeth 1232 of worm drive 1230, according to an exemplary embodiment. To facilitate engagement between worm drive 1230 and lever 1240, head 1242 of lever 1240 may comprise gear teeth 1244 complementary to gear teeth 1232 of worm drive 1230. Gear housing 1222 may comprise projections 1224, as shown in the exemplary embodiment of FIGS. 17 and 18, which guide movement of head 1242 along a general proximal-distal direction and minimize or prevent movement of head 1242 along lateral directions indicated by arrows 1254 in the exemplary embodiment of FIG. 18. Thus, instead of worm drive 1230 comprising a threaded section and grooves and lever 1240 including a follower disposed within a grooves, as described above for the worm drive 330 and lever 340 of the exemplary embodiment of FIGS. 3-7, worm drive 1230 and lever 1240 may engage one another via respective gear teeth 1232, 1244.

Figure 17:
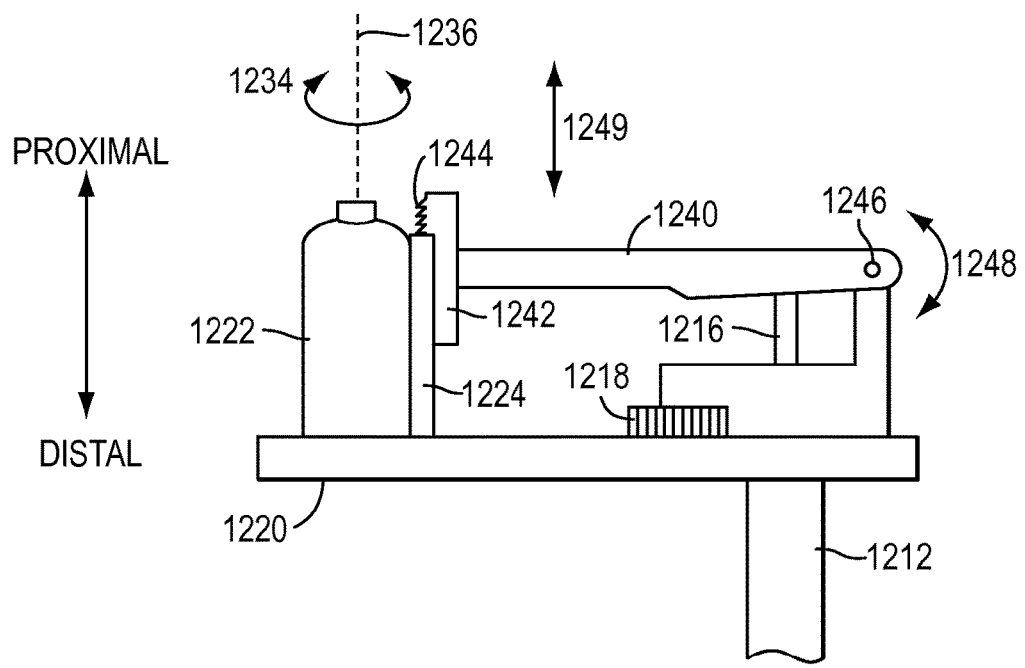
FIG. 17 is a side view of a proximal portion of the surgical instrument of FIG. 16.
Figure 18:
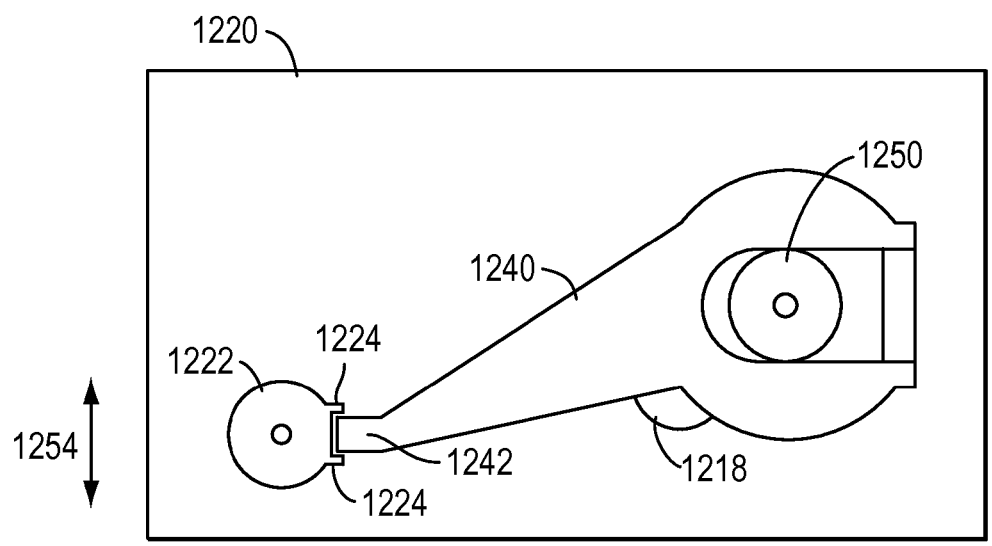
FIG. 18 is a top view of the proximal portion of the surgical instrument of FIG. 16.

Lever 1240 may further be coupled to chassis 1220 via a pin 1246, as shown in the exemplary embodiment of FIGS. 16 and 17. Further, lever 1240 may be coupled to actuation element 1216 via a coupler 1250 connected to actuation element 1216, as discussed above with regard to the exemplary embodiments of FIGS. 3-7 and 14. Worm drive 1230 is configured to rotate about axis 1236 when worm drive 1230 is driven by input from an actuation interface assembly (not shown, but can be, e.g., actuation interface assembly 122 of FIG. 1), such as in the directions indicated by arrows 1234 in the exemplary embodiment of FIGS. 16 and 17.

Due to the engagement between worm drive 1230 and lever 1240, and because lever 1240 is pivotably mounted to chassis 1220 via pin 1246, head 1242 of lever 1240 may follow a generally arcuate path, such as by pivoting about pin 1246 in the directions indicated by arrows 1248 in the exemplary embodiment of FIG. 17. According to an exemplary embodiment, the curvature of the arcuate path may be sufficiently large so that the motion of lever 1240, such as at head 1242, is a generally linear motion along the directions indicated by arrows 1249 in the exemplary embodiment of FIG. 17. As indicated by arrows 1249 in FIG. 17, the movement of actuation element 1216 may be a generally linear movement, such as along a proximal-distal direction of shaft 1212. Thus, force transmission mechanism 1210, including worm drive 1230 and lever 1240, may function to translate a rotational movement of worm drive 1230 into a linear movement of actuation element 1216. As a result, a surgical instrument may be may be efficiently actuated (e.g., by actuating end effector 220 in the exemplary embodiment of FIG. 2) by force transmission mechanism 1210 with low friction and a substantial torque.

The various components of the force transmission mechanisms of the exemplary embodiments described herein may be manufactured via a molding process, according to an exemplary embodiment. For example, the worm drive, the lever or link, coupler connecting a lever to an actuation element, and/or chassis may each be manufactured by a molding process. Force transmission mechanism components manufactured via a molding process may be made of a plastic material. For example, a worm drive of the various exemplary embodiments described herein may be made of a plastic, such as, for example, a polyamide (e.g., 10% glass filled nylon). In another example, a coupler may be made of a plastic, such as, for example, polyetherimide (PEI). A lever arm (e.g. lever arm 340 of FIG. 3) may be made of, for example, PEI, such as 10% glass filled PEI. A chassis (e.g., chassis 320 in FIG. 4) may be made of, for example, polycarbonate, such as 30% glass filled polycarbonate.

The exemplary embodiments and methods described herein have been described as being utilized with surgical instruments for teleoperated surgical systems. However, the exemplary embodiments and methods described herein may be used with other surgical devices, such as laparoscopic instruments and other hand held instruments. Further, the exemplary embodiments and methods may be employed in other application that use remotely actuatable wrist or multiple joint structures, such as to remotely position an object attached to the wrist or joint structures. For instance, the exemplary embodiments described herein may be used in devices used for pipe inspection and other devices utilizing remote access via teleoperation or manual actuation.

By providing a force transmission mechanism comprising a worm drive connected to an actuation element, both rotational and translational movement of an actuation element of a surgical instrument may be permitted while providing an efficient means of translating force from the worm drive to the actuation element, which may be used to actuated a surgical instrument including the force transmission mechanism.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the claims being entitled to their full breadth and scope, including equivalents.

What is claimed is:

1. A surgical instrument, comprising:
   a shaft comprising a proximal end portion and a distal end portion,
   an end effector coupled to the distal end portion of the shaft, and
   a force transmission mechanism;
   wherein the force transmission mechanism comprises a chassis, a worm drive, a lever arm, and an actuation element;
   wherein the lever arm comprises a first end portion, a second end portion, an intermediate portion extending between the first end portion and the second end portion, and a follower member at the first end portion of the lever arm;
   wherein the follower member is engaged with and driven by the worm drive;
   wherein the lever arm is pivotable about a pivot axis at the second end portion of the lever arm;
   wherein the actuation element operably couples the lever arm and the end effector;

wherein the actuation element is coupled to the lever arm at a location on the intermediate portion of the lever arm between the follower member and the pivot axis; and wherein the follower member is drivable by rotational movement of the worm drive such that the rotational movement of the worm drive imparts pivoting movement to the lever arm about the pivot axis and translational movement to the actuation element via the lever arm.

2. The surgical instrument of claim 1, wherein the worm drive comprises a threaded section defining a spiral groove between thread portions of the threaded section, and the follower member is received within the spiral groove of the worm drive.

3. The surgical instrument of claim 2, wherein the threaded section comprises a central section and axial surfaces having a slope ranging from 10 degrees to 60 degrees.

4. The surgical instrument of claim 2, wherein the spiral groove is wider at an outer radial surface of the worm drive than at a central section of the worm drive.

5. The surgical instrument of claim 2, wherein the spiral groove is wider at a central section of the worm drive than at an outer radial surface of the worm drive.

6. The surgical instrument of claim 2, wherein the follower member comprises a roller.

7. The surgical instrument of claim 2, wherein the follower member comprises a pin.

8. The surgical instrument of claim 2, wherein the follower member comprises a ball.

9. The surgical instrument of claim 1, wherein the actuation element is a push/pull drive element.

10. The surgical instrument of claim 1, wherein the surgical instrument is a non-wristed instrument.

11. The surgical instrument of claim 1, further comprising a roll gear rotatably coupling the shaft relative to the chassis.

12. The surgical instrument of claim 1,
wherein the worm drive comprises gear teeth;
wherein the follower member comprises an engagement head; and
wherein the engagement head comprises gear teeth engaged with the gear teeth of the worm drive.

13. The surgical instrument of claim 1, wherein the translational movement imparted to the actuation element by the worm drive is translational movement along an axial direction of the shaft.

14. The surgical instrument of claim 1, wherein the force transmission mechanism comprises a coupler that couples the actuation element to the lever arm, the coupler being rotatable relative to the lever arm.

15. The surgical instrument of claim 1, wherein the lever arm and the worm drive are coupled to a first face of the chassis, the proximal end portion of the shaft is coupled to a second face of the chassis opposite from the first face, and the actuation element extends from the lever arm through the chassis into the shaft.

16. An instrument, comprising:
a shaft comprising a proximal end portion and a distal end portion;
a jaw assembly coupled to the distal end portion of the shaft; and
a force transmission mechanism coupled to the proximal end portion of the shaft, the force transmission mechanism comprising a worm drive, a lever arm, and an actuation element, the lever arm comprising a follower member engaged with and driven by the worm drive, the actuation element operably coupling the lever arm and the jaw assembly;
wherein the lever arm is pivotable about a pivot axis in response to rotational movement of the worm drive;
the lever arm comprises an intermediate portion extending between the pivot axis and the follower member;
wherein the actuation element is coupled to the lever arm at a location on the intermediate portion of the lever arm between the follower member and the pivot axis, and
wherein the rotational movement of the worm drive imparts, via pivotable movement of the lever arm about the pivot axis, translational movement to the actuation element to actuate opening and closing of the jaw assembly.

17. The instrument of claim 16, wherein the actuation element comprises a push/pull drive element.

18. The instrument of claim 16, wherein the translational movement imparted to the actuation element by the worm drive to actuate opening and closing of the jaw assembly is translational movement along an axial direction of the shaft.

19. The instrument of claim 16, wherein the force transmission mechanism comprises a coupler that couples the actuation element to the lever arm, the coupler being rotatable relative to the lever arm.

20. The instrument of claim 16, wherein the force transmission mechanism comprises a chassis wall, the lever arm and the worm drive are coupled to a first face of the chassis wall, the proximal end portion of the shaft is coupled to a second face of the chassis wall opposite from the first face, and the actuation element extends from the lever arm through the chassis wall into the shaft.

* * * * *